(12) United States Patent
Leven et al.

(10) Patent No.: US 10,716,935 B2
(45) Date of Patent: Jul. 21, 2020

(54) ELECTRICAL STIMULATION LEADS, SYSTEMS AND METHODS FOR STIMULATION OF DORSAL ROOT GANGLIA

(71) Applicant: Boston Scientific Neuromodulation Corporation, Valencia, CA (US)

(72) Inventors: Jacob B. Leven, Huntington Beach, CA (US); Anne M. Pianca, Santa Monica, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 151 days.

(21) Appl. No.: 15/799,120

(22) Filed: Oct. 31, 2017

(65) Prior Publication Data

US 2018/0126152 A1 May 10, 2018

Related U.S. Application Data

(60) Provisional application No. 62/417,782, filed on Nov. 4, 2016.

(51) Int. Cl.
*A61N 1/05* (2006.01)

(52) U.S. Cl.
CPC ................. *A61N 1/0551* (2013.01)

(58) Field of Classification Search
CPC ..................... A61N 1/0551; A61N 1/0553
See application file for complete search history.

(56) References Cited

U.S. PATENT DOCUMENTS

| | | | |
|---|---|---|---|
| 3,333,045 A | 7/1967 | Fisher et al. | |
| 3,918,440 A | 11/1975 | Kraus | |
| 4,046,151 A * | 9/1977 | Rose | A61N 1/0573 607/127 |
| 5,143,090 A | 9/1992 | Dutcher et al. | |
| 5,217,028 A | 6/1993 | Dutcher et al. | |
| 5,330,477 A | 7/1994 | Crook | |
| 5,738,521 A | 4/1998 | Dugot | |
| 5,876,431 A | 3/1999 | Spehr et al. | |
| 6,104,957 A | 8/2000 | Alo et al. | |
| 6,181,969 B1 | 1/2001 | Gord | |
| 6,516,227 B1 | 2/2003 | Meadows et al. | |
| 6,609,029 B1 | 8/2003 | Mann et al. | |

(Continued)

FOREIGN PATENT DOCUMENTS

| | | |
|---|---|---|
| AU | 2012201634 A1 | 4/2012 |
| WO | 2003020365 A1 | 3/2003 |

(Continued)

*Primary Examiner* — Joseph M Dietrich
(74) *Attorney, Agent, or Firm* — Lowe Graham Jones PLLC; Bruce E. Black

(57) ABSTRACT

An implantable electrical stimulation lead includes a lead body having a proximal portion and a distal portion; electrodes disposed along the distal portion of the lead body; terminals disposed along the proximal portion of the lead body; conductor extending along the lead body and electrically coupling the electrodes to the terminals; and a flexible hinge forming part of the distal portion of the lead body and disposed proximal to the electrodes, wherein the flexible hinge is structurally distinguishable from adjacent regions of the lead body and more flexible than the adjacent regions.

20 Claims, 14 Drawing Sheets

(56) References Cited

U.S. PATENT DOCUMENTS

| | | |
|---|---|---|
| 6,609,032 B1 | 8/2003 | Woods et al. |
| 6,741,892 B1 | 5/2004 | Meadows et al. |
| 6,902,547 B2 | 6/2005 | Aves et al. |
| 7,244,150 B1 | 7/2007 | Brase et al. |
| 7,337,005 B2 | 2/2008 | Kim et al. |
| 7,337,006 B2 | 2/2008 | Kim et al. |
| 7,437,193 B2 | 10/2008 | Parramon et al. |
| 7,447,546 B2 | 11/2008 | Kim et al. |
| 7,450,993 B2 | 11/2008 | Kim et al. |
| 7,450,997 B1 | 11/2008 | Pianca et al. |
| 7,502,651 B2 | 3/2009 | Kim et al. |
| 7,580,753 B2 | 8/2009 | Kim et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 7,993,378 B2 | 8/2011 | Foley et al. |
| 8,082,039 B2 | 12/2011 | Kim et al. |
| 8,175,710 B2 | 5/2012 | He |
| 8,204,595 B2 | 6/2012 | Pianca et al. |
| 8,224,450 B2 | 7/2012 | Brase |
| 8,229,565 B2 | 7/2012 | Kim et al. |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmerman et al. |
| 8,647,346 B2 | 2/2014 | Bleich et al. |
| 8,688,235 B1 | 4/2014 | Pianca et al. |
| 8,712,546 B2 | 4/2014 | Kim et al. |
| 8,768,488 B2 | 7/2014 | Barker |
| 8,774,926 B2 | 7/2014 | Alataris et al. |
| 8,831,742 B2 | 9/2014 | Pianca et al. |
| 8,897,893 B2 | 11/2014 | Pianca |
| 8,983,624 B2 | 3/2015 | Imran |
| 9,089,694 B2 | 7/2015 | Pianca |
| 9,199,074 B2 | 12/2015 | Pianca |
| 9,205,259 B2 | 12/2015 | Kim et al. |
| 9,205,260 B2 | 12/2015 | Kim et al. |
| 9,259,569 B2 | 2/2016 | Brounstein et al. |
| 2005/0033374 A1 | 2/2005 | Gerber |
| 2005/0240238 A1 | 10/2005 | Mamo et al. |
| 2007/0150036 A1 | 6/2007 | Anderson |
| 2007/0239248 A1 | 10/2007 | Hastings et al. |
| 2007/0265682 A1 | 11/2007 | Wiegnann et al. |
| 2008/0071320 A1 | 3/2008 | Brase |
| 2008/0140152 A1 | 6/2008 | Imran et al. |
| 2008/0140153 A1 | 6/2008 | Burdulis |
| 2008/0140169 A1 | 6/2008 | Imran |
| 2008/0262588 A1 | 10/2008 | Zarembo et al. |
| 2009/0187222 A1 | 7/2009 | Barker |
| 2009/0204193 A1 | 8/2009 | Kokones et al. |
| 2009/0276021 A1 | 11/2009 | Meadows et al. |
| 2009/0276025 A1 | 11/2009 | Burnes et al. |
| 2010/0057177 A1* | 3/2010 | Moffitt ............... A61N 1/0553 607/117 |
| 2010/0076535 A1 | 3/2010 | Pianca et al. |
| 2010/0137938 A1 | 6/2010 | Kishawi et al. |
| 2010/0179562 A1 | 7/2010 | Linker et al. |
| 2010/0241179 A1 | 9/2010 | Gielen et al. |
| 2010/0249875 A1 | 9/2010 | Kishawi et al. |
| 2010/0268298 A1 | 10/2010 | Moffitt et al. |
| 2010/0274336 A1 | 10/2010 | Nguyen-Stella et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0213445 A1 | 9/2011 | Blischak |
| 2011/0238129 A1 | 9/2011 | Moffitt et al. |
| 2011/0276056 A1 | 11/2011 | Grigsby et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0101326 A1 | 4/2012 | Simon et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0184799 A1* | 7/2013 | Kipke ............... A61N 1/05 607/118 |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |
| 2013/0325091 A1 | 12/2013 | Pianca et al. |
| 2014/0018885 A1 | 1/2014 | Pianca |
| 2014/0039587 A1 | 2/2014 | Romero |
| 2014/0257240 A1 | 9/2014 | Burdulis |
| 2014/0276925 A1 | 9/2014 | Alves et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0099936 A1 | 4/2015 | Burdulis et al. |
| 2015/0151113 A1 | 6/2015 | Govea et al. |
| 2015/0374978 A1* | 12/2015 | Howard ............... A61N 1/08 607/116 |
| 2017/0333702 A1 | 11/2017 | Barner |
| 2018/0021569 A1 | 1/2018 | Pianca |

FOREIGN PATENT DOCUMENTS

| | | |
|---|---|---|
| WO | 2003084398 A1 | 10/2003 |
| WO | 2005120203 A2 | 12/2005 |
| WO | 2006029257 A2 | 3/2006 |
| WO | 2007041604 A2 | 4/2007 |
| WO | 2010083308 A1 | 7/2010 |

* cited by examiner

ELECTRICAL STIMULATION LEADS, SYSTEMS AND METHODS FOR STIMULATION OF DORSAL ROOT GANGLIA

CROSS-REFERENCE TO RELATED APPLICATIONS

This application claims the benefit under 35 U.S.C. § 119(e) of U.S. Provisional Patent Application Ser. No. 62/417,782, filed Nov. 4, 2016, which is incorporated herein by reference.

FIELD

The present invention is directed to the area of implantable electrical stimulation systems and methods of making and using the systems. The present invention is also directed to electrical stimulation leads, systems, and methods for stimulation of dorsal root ganglia and other body tissues.

BACKGROUND

Implantable electrical stimulation systems have proven therapeutic in a variety of diseases and disorders. For example, spinal cord stimulation systems have been used as a therapeutic modality for the treatment of chronic pain syndromes. Sacral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Dorsal root ganglia are nodules of cell bodies disposed along the dorsal roots of spinal nerves. Dorsal root ganglia are usually (although not always) disposed external to the epidural space. Dorsal root ganglia, however, are disposed in proximity to the spinal cord and the vertebral column.

BRIEF SUMMARY

One embodiment is an implantable electrical stimulation lead that includes a lead body having a proximal portion and a distal portion; electrodes disposed along the distal portion of the lead body; terminals disposed along the proximal portion of the lead body; conductor extending along the lead body and electrically coupling the electrodes to the terminals; and a flexible hinge forming part of the distal portion of the lead body and disposed proximal to the electrodes, wherein the flexible hinge is structurally distinguishable from adjacent regions of the lead body and more flexible than the adjacent regions.

In at least some embodiments, the flexible hinge is formed of a lower durometer material than the adjacent regions of the lead body. In at least some embodiments, the flexible hinge is formed of a different, more flexible material than the adjacent regions of the lead body. In at least some embodiments, the conductors extend straight along the lead body except along the flexible hinge where the conductors are coiled.

In at least some embodiments, the lead body includes a jacket and a multi-lumen conductor guide disposed within the jacket, the multi-lumen conductor guide extending from the proximal portion to the distal portion of the lead body and defining a plurality of conductor lumen through which the conductors extend. In at least some embodiments, in the flexible hinge, the multi-lumen conductor guide includes an outer portion and an inner portion that are separate from each other and can move relative to each other, wherein, in the adjacent regions of the lead body, the multi-lumen conductor guide has a single-piece construction. In at least some embodiments, in the flexible hinge, the jacket has a bellows-like construction and, in the adjacent regions, the jacket does not have a bellows-like construction.

In at least some embodiments, the lead body includes a jacket and a conductor guide disposed within the jacket and extending from the proximal portion to the distal portion of the lead body, where, in the flexible hinge, the conductor guide includes two concentric tubes with the conductors disposed between the two concentric tubes and, in the adjacent regions of the lead body, the conductor guide defines a plurality of conductor lumen through which the conductors extend.

In at least some embodiments, the lead body has at least one cut in an outer wall of the lead body along the flexible hinge, wherein the lead body is not cut in the adjacent regions of the lead body. In at least some embodiments, the lead further includes at least one stiffening element in the adjacent regions of the lead body and no stiffening element in the flexible hinge. In at least some embodiments, the conductors are coiled and extend along the lead body, wherein in the flexible hinge a pitch of the coiled conductors is wider than in the adjacent regions.

In at least some embodiments, the electrodes include segmented electrodes. In at least some embodiments, at least part of the distal portion of the lead body upon which the electrodes are disposed is flat.

In at least some embodiments, the distal portion of the lead body includes a trough-like region within which the electrodes are disposed. In at least some embodiments, the trough-like region is configured and arranged to fit over a portion of a dorsal root ganglion. In at least some embodiments, the electrodes include segmented electrodes arranged in sets of two or more segmented electrodes with each set disposed at a different longitudinal position along the distal portion of the lead body.

Another embodiment is a method for implanting any of the leads described above for stimulation of a dorsal root ganglion of a patient. The method includes advancing the distal portion of the lead using an introducer into an epidural space of the patient and through a foramen of the patient to a position near the dorsal root ganglion; bending the lead at the flexible hinge; and removing the introducer. In at least some embodiments, the method further includes retracting the introducer to expose the flexible hinge prior to bending the lead at the flexible hinge.

A further embodiment is a system for electrical stimulation that includes any of the leads described above; and a control module electrically coupleable to the lead. In at least some embodiments, the system further includes a lead extension electrically coupleable between the lead and the control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to electrical stimulation leads, systems, and methods for stimulation of dorsal root ganglia and other body tissues.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181, 969; 6,516,227; 6,609,029; 6,609,032; 6,741,892; 7,244, 150; 7,450,997; 7,672,734; 7,761,165; 7,783,359; 7,792, 590; 7,809,446; 7,949,395; 7,974,706; 8,175,710; 8,224, 450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1A:
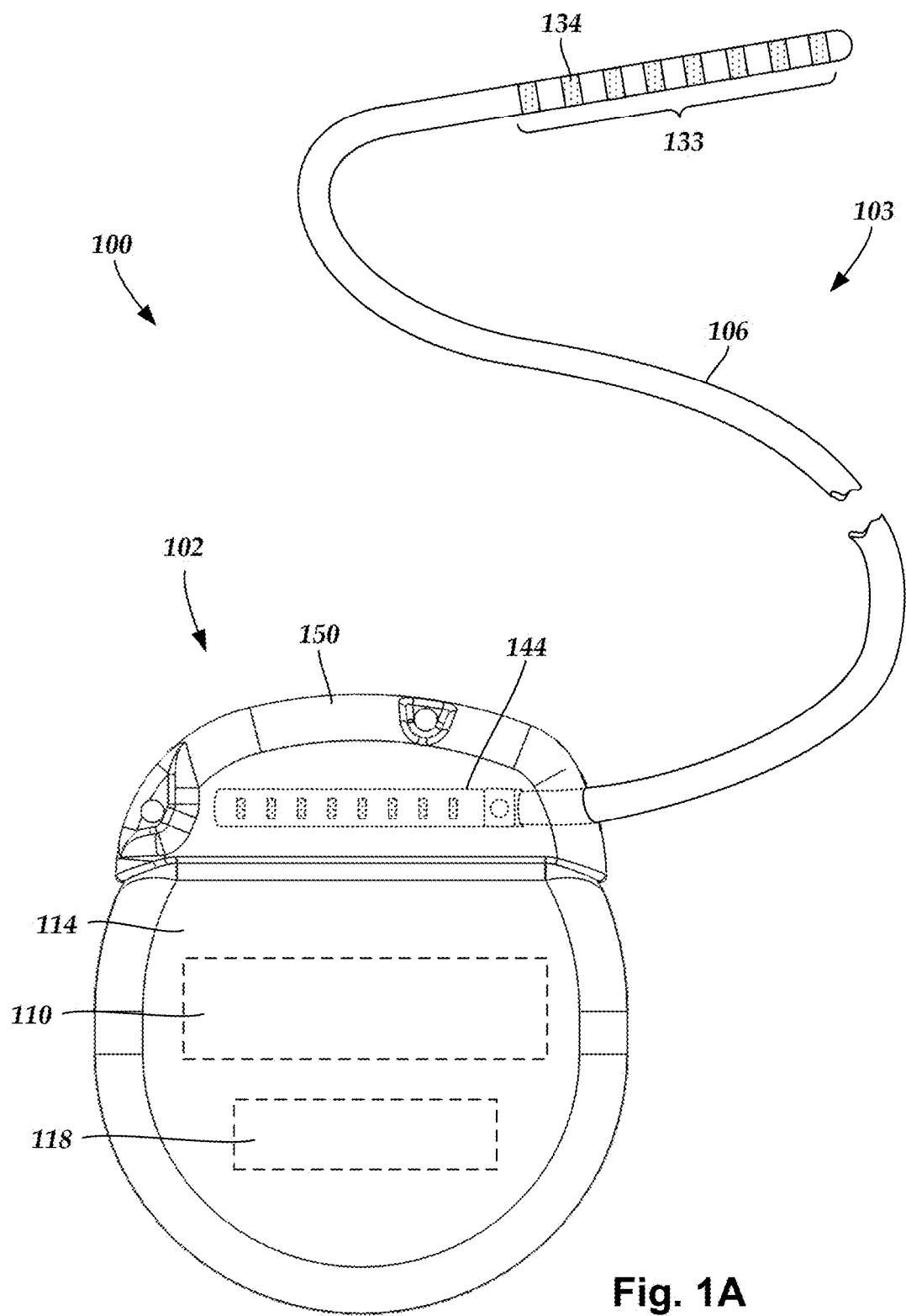
FIG. 1A is a schematic view of another embodiment of an electrical stimulation system that includes a percutaneous lead body coupled to a control module, according to the invention.

FIG. 1A illustrates schematically one embodiment of an electrical stimulation system 100. The electrical stimulation system 100 includes a control module (e.g., a stimulator or pulse generator) 102 and a percutaneous lead 103. The lead 103 includes a plurality of electrodes 134 that form an array of electrodes 133. The control module 102 typically includes an electronic subassembly 110 and an optional power source 118 disposed in a sealed housing 114. The lead 103 includes a lead body 106 coupling the control module 102 to the plurality of electrodes 134. In at least some embodiments, the lead body 106 is isodiametric.

The control module 102 typically includes one or more connector assemblies 144 into which the proximal end of the lead body 106 can be plugged to make an electrical connection via connector contacts (e.g., 216 in FIG. 2A) disposed in the connector assembly 144 and terminals (e.g., 210 in FIG. 2A) disposed along the lead body 106. The connector contacts are coupled to the electronic subassembly 110 and the terminals are coupled to the electrodes 134. Optionally, the control module 102 may include a plurality of connector assemblies 144.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions (not shown) can be disposed between the lead body 106 and the control module 102 to extend the distance between the lead body 106 and the control module 102.

The electrical stimulation system or components of the electrical stimulation system, including the lead body 106 and the control module 102, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, or titanium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1A, eight electrodes 134 are shown. The electrodes 134 can be formed in any suitable shape including, for example, round, oval, triangular, rectangular, pentagonal, hexagonal, heptagonal, octagonal, or the like. In the illustrated leads, the electrodes are ring electrodes. Any number of ring electrodes can be disposed along the length of the lead body including, for example, one, two three, four, five, six, seven, eight, nine, ten, eleven, twelve, thirteen, fourteen, fifteen, sixteen or more ring electrodes. It will be understood that any number of ring electrodes can be disposed along the length of the lead body.

Figure 1B:
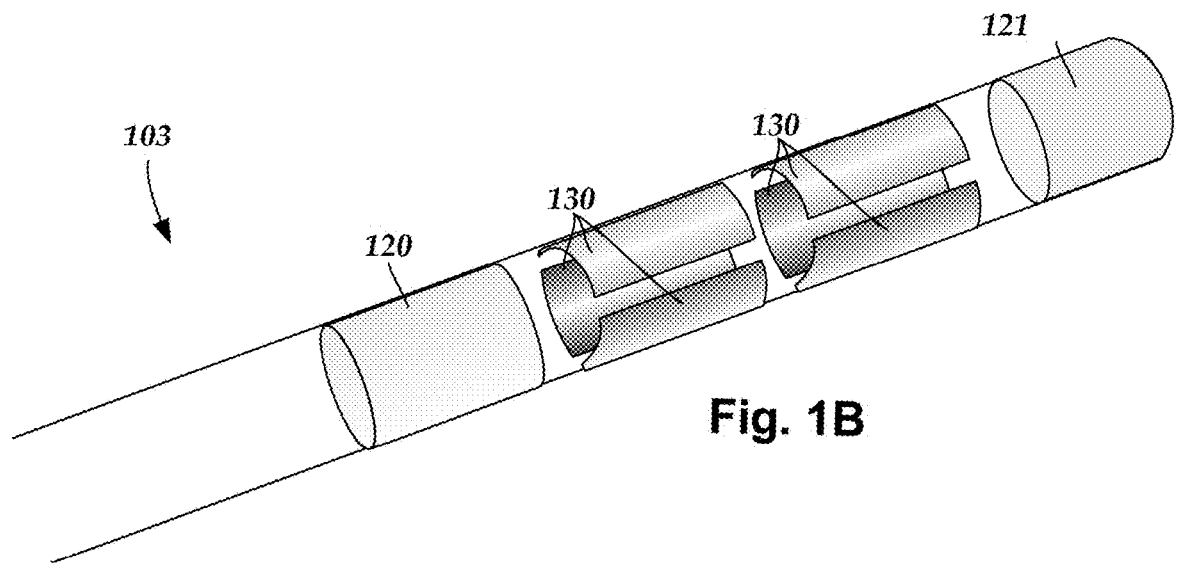
FIG. 1B is a schematic perspective view of the distal portion of another embodiment of a lead with segmented electrodes, according to the invention.

FIG. 1B illustrates a distal end of a lead 103 with a ring electrode 120, a tip electrode 121, and six segmented electrodes 130. Segmented electrodes may provide for superior current steering than ring electrodes because target structures may not be disposed symmetrically about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to target tissue, while potentially avoiding stimulation of other tissue.

Examples of leads with segmented electrodes include U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. Examples of leads with tip electrodes include at least some of the previously cited references, as well as U.S. Patent Applications Publication Nos. 2014/0296953 and 2014/0343647, all of which are incorporated herein by reference in their entireties. A lead with segmented electrodes may be a directional lead that can provide stimulation in a particular direction using the segmented electrodes.

Any number of segmented electrodes 130 may be disposed on the lead body including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 103 at a particular longitudinal portion of the lead 103. The lead 102 may have any number segmented electrodes 130 in a given set of segmented electrodes. The lead 103 may have one, two, three, four, five, six, seven, eight, or more segmented electrodes 130 in a given set. The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 103) may be identical in size and shape.

Each set of segmented electrodes 130 may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the lead 103. In at least some embodiments, equal spaces, gaps or cutouts are disposed between each segmented electrode 130 around the circumference of the lead body. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body.

The electrodes of the lead body 106 are typically disposed in, or separated by, a non-conductive, biocompatible material including, for example, silicone, polyurethane, and the like or combinations thereof. The lead body 106 may be formed in the desired shape by any process including, for example, extruding, molding (including injection molding), casting, and the like. Electrodes and connecting wires can be disposed onto or within a lead body either prior to or subsequent to a molding or casting process. The non-conductive material typically extends from the distal end of the lead body 106 to the proximal end of the lead body 106.

Terminals (e.g., 210 in FIG. 2A) are typically disposed at the proximal end of the lead body 106 for connection to corresponding conductive contacts (e.g., 216 in FIG. 2A) in one or more connector assemblies (e.g., 144 in FIG. 1A) disposed on, for example, the control module 102 (or to other devices, such as conductive contacts on a lead extension, an operating room cable, a splitter, an adaptor, or the like).

Conductive wires extend from the plurality of terminals (see e.g., 210 in FIG. 2A) to the plurality of electrodes 133. Typically, each of the plurality of terminals is electrically coupled to at least one of the plurality of electrodes 133. In some embodiments, each of the plurality of terminals is coupled to a single electrode 134 of the plurality of electrodes 133.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the lead 103. The one or more lumens may, optionally, be flushed continually, or on a regular basis, with saline or the like. The one or more lumens can be permanently or removably sealable at the distal end.

As discussed above, the lead body 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1A, the lead body 106 includes eight terminals that are shown coupled with eight conductive contacts disposed in the connector assembly 144.

Figure 2A:
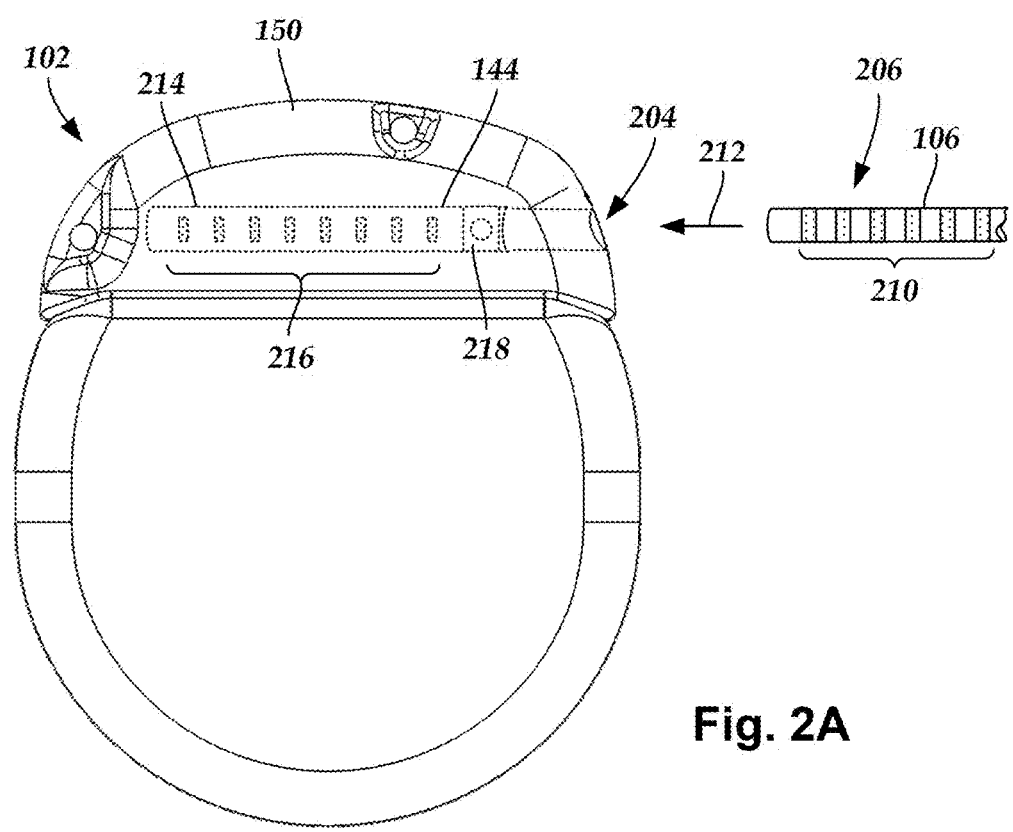
FIG. 2A is a schematic view of one embodiment of a plurality of connector assemblies disposed in the control module of FIG. 1A, the connector assemblies configured and arranged to receive the proximal portions of the lead bodies of FIG. 1A, according to the invention.

FIG. 2A is a schematic side view of one embodiment of a connector assembly 144 disposed on the control module 102. In FIG. 2A, the proximal end 206 of the lead body 106 is shown configured and arranged for insertion to the control module 102.

In FIG. 2A, the connector assembly 144 is disposed in the header 150. In at least some embodiments, the header 150 defines a port 204 into which the proximal end 206 of the lead body 106 with terminals 210 can be inserted, as shown by directional arrows 212, in order to gain access to the connector contacts disposed in the connector assembly 144.

The connector assembly 144 includes a connector housing 214 and a plurality of connector contacts 216 disposed therein. Typically, the connector housing 214 defines a port (not shown) that provides access to the plurality of connector contacts 216. In at least some embodiments, the connector assembly 144 further includes a retaining element 218 configured and arranged to fasten the corresponding lead body 106 or lead retention sleeve to the connector assembly 144 when the lead body 106 is inserted into the connector assembly 144 to prevent undesired detachment of the lead body 106 from the connector assembly 144. For example, the retaining element 218 may include an aperture 220 through which a fastener (e.g., a set screw, pin, or the like) may be inserted and secured against an inserted lead body 106 or lead retention sleeve.

When the lead body 106 is inserted into the port 204, the connector contacts 216 can be aligned with the terminals 210 disposed on the lead body 106 to electrically couple the control module 102 to the electrodes (134 of FIG. 1A) disposed at a distal end of the lead body 106. Examples of connector assemblies in control modules are found in, for example, U.S. Pat. No. 7,244,150 and U.S. Patent Application Publication No. 2008/0071320, which are incorporated by reference.

Figure 2B:
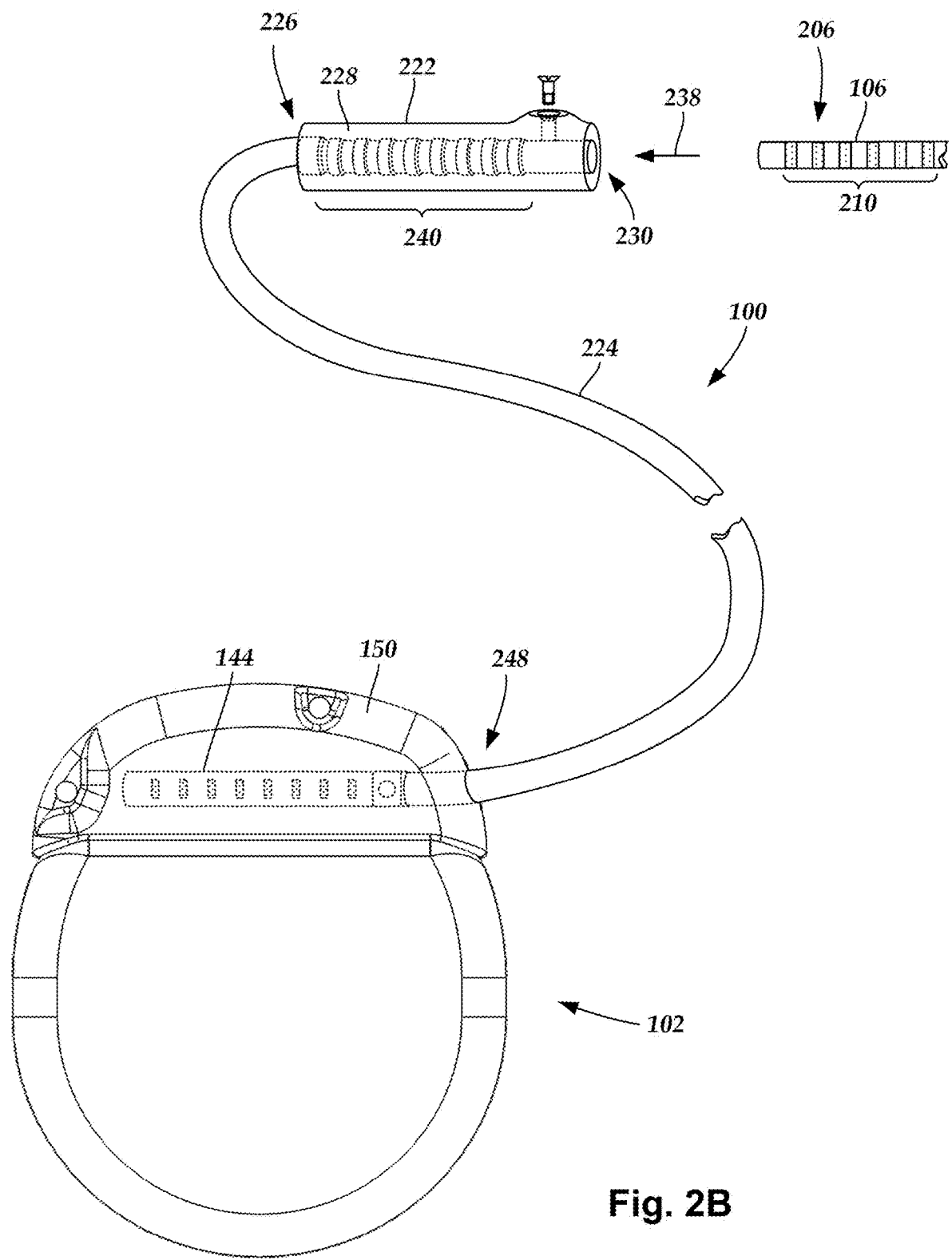
FIG. 2B is a schematic view of one embodiment of a proximal portion of the lead body of FIG. 1, a lead extension, and the control module of FIG. 1A, the lead extension configured and arranged to couple the lead body to the control module, according to the invention.

In at least some embodiments, the electrical stimulation system includes one or more lead extensions. The lead body 106 can be coupled to one or more lead extensions which, in turn, are coupled to the control module 102. In FIG. 2B, a lead extension connector assembly 222 is disposed on a lead extension 224. The lead extension connector assembly 222 is shown disposed at a distal end 226 of the lead extension 224. The lead extension connector assembly 222 includes a contact housing 228. The contact housing 228 defines at least one port 230 into which a proximal end 206 of the lead body 106 with terminals 210 can be inserted, as shown by directional arrow 238. The lead extension connector assembly 222 also includes a plurality of connector contacts 240. When the lead body 106 is inserted into the port 230, the connector contacts 240 disposed in the contact housing 228 can be aligned with the terminals 210 on the lead body 106 to electrically couple the lead extension 224 to the electrodes (134 of FIG. 1A) disposed at a distal end (not shown) of the lead body 106.

The proximal end of a lead extension can be similarly configured and arranged as a proximal end of a lead body. The lead extension 224 may include a plurality of conductive wires (not shown) that electrically couple the connector contacts 240 to terminal on a proximal end 248 of the lead extension 224. The conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a lead extension connector assembly disposed in another lead extension. In other embodiments (as shown in FIG. 2B), the proximal end 248 of the lead extension 224 is configured and arranged for insertion into the connector assembly 144 disposed on the control module 102.

Figure 3A:
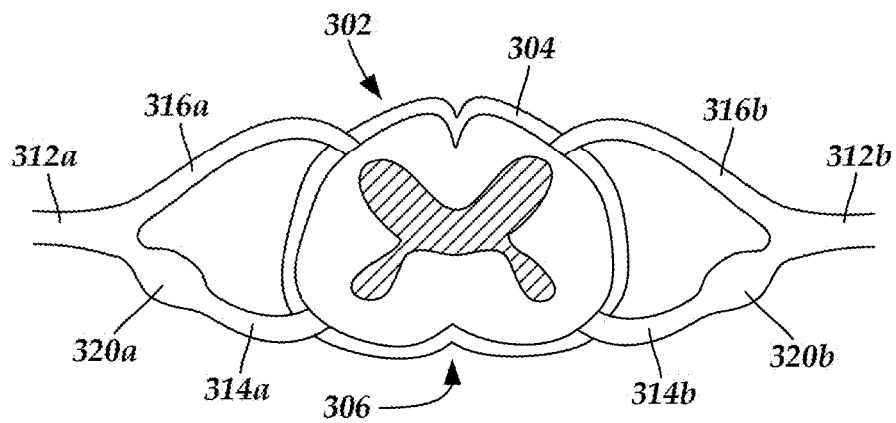
FIG. 3A is a schematic transverse cross-sectional view of spinal nerves extending from a spinal cord, the spinal nerves including dorsal root ganglia.

Turning to FIG. 3A, in at least some embodiments one or more dorsal root ganglia ("DRG") are potential target stimulation locations. FIG. 3A schematically illustrates a transverse cross-sectional view of a spinal cord 302 surrounded by dura 304. The spinal cord 302 includes a midline 306 and a plurality of levels from which spinal nerves 312a and 312b extend. In at least some spinal cord levels, the spinal nerves 312a and 312b extend bilaterally from the midline 306 of the spinal cord 302. In FIG. 3A, the spinal nerves 312a and 312b are shown attaching to the spinal cord 302 at a particular spinal cord level via corresponding dorsal roots 314a and 314b and corresponding ventral (or anterior) roots 316a and 316b. Typically, the dorsal roots 314a and 314b relay sensory information into the spinal cord 302 and the ventral roots 316a and 316b relay motor information outward from the spinal cord 302. The DRG 320a and 320b are nodules of cell bodies that are disposed along the dorsal roots 316a and 316b in proximity to the spinal cord 302.

Figure 3B:
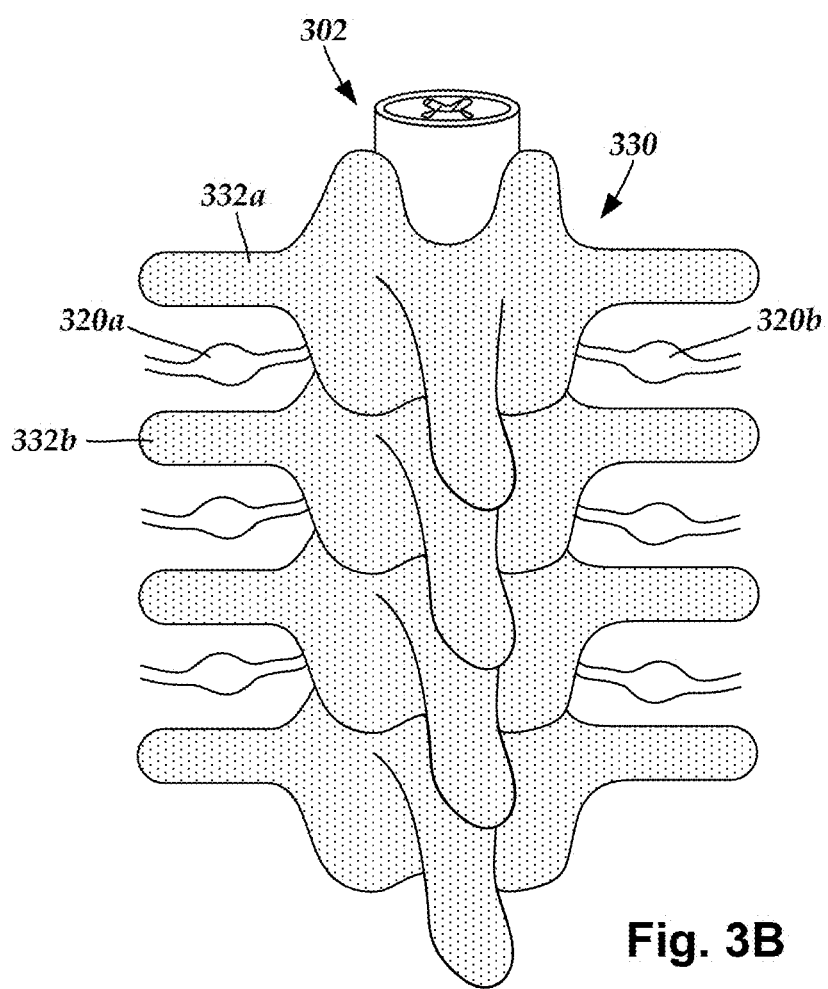
FIG. 3B is a schematic perspective view of a portion of the spinal cord of FIG. 3A disposed in a portion of a vertebral column with the dorsal root ganglia of FIG. 3A extending outward from the vertebral column.

FIG. 3B schematically illustrates a perspective view of a portion of the spinal cord 302 disposed along a portion of a vertebral column 330. The vertebral column 330 includes stacked vertebrae, such as vertebrae 332a and 332b, and a plurality of DRGs 320a and 320b extending outwardly bilaterally from the spinal cord 302 at different spinal cord levels.

Figure 3C:
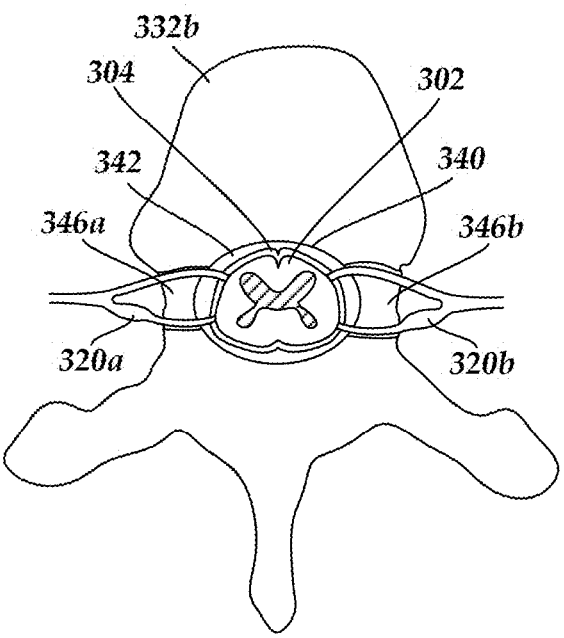
FIG. 3C is a schematic top view of a portion of the spinal cord of FIG. 3A disposed in a vertebral foramen defined in a vertebra of the vertebral column of FIG. 3B, the vertebra also defining intervertebral foramina extending between an outer surface of the vertebra and the vertebral foramen, the intervertebral foramina providing an opening through which the dorsal root ganglia of FIG. 3B can extend outward from the spinal cord of FIG. 3B.

FIG. 3C schematically illustrates a top view of a portion of the spinal cord 302 and surrounding dura 304 disposed in a vertebral foramen 340 defined in the vertebra 332b. The vertebrae, such as the vertebrae 332a and 332b, are stacked together and the vertebral foramina 340 of the vertebrae collectively form a spinal canal through which the spinal cord 302 extends. The space within the spinal canal between the dura 304 and the walls of the vertebral foramen 340 defines the epidural space 342. Intervertebral foramina 346a and 346b, defined bilaterally along sides of the vertebra 332b, form openings through the vertebra 332b between the epidural space 342 and the environment external to the vertebra 332b.

Figure 3D:
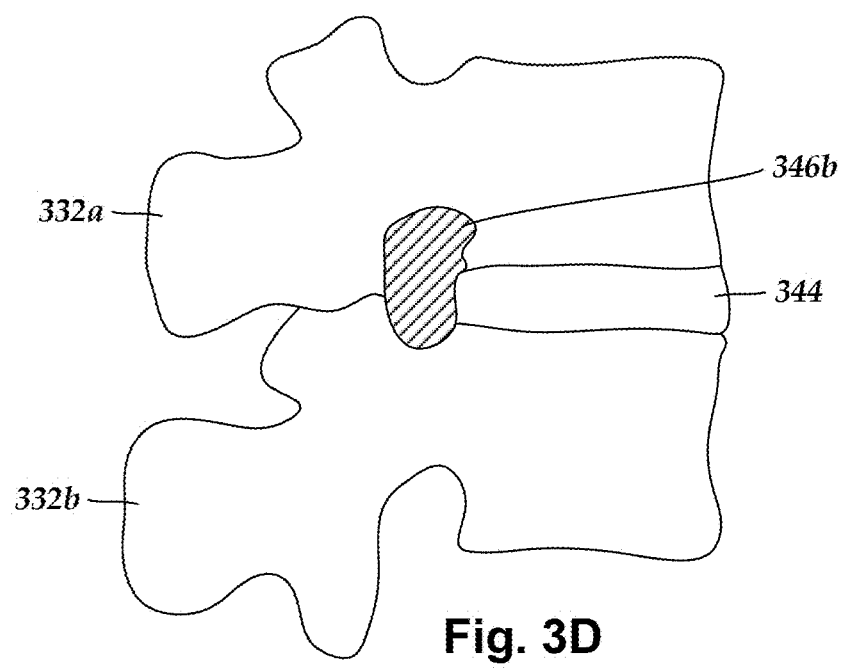
FIG. 3D is a schematic side view of two vertebrae of the vertebral column of FIG. 3B, the vertebrae defining an intervertebral foramen through which one of the dorsal root ganglia of FIG. 3B can extend outward from the spinal cord of FIG. 3B.

FIG. 3D schematically illustrates a side view of two vertebrae 332a and 332b coupled to one another by a disc 344. In FIG. 3D, the intervertebral foramen 346b is shown defined between the vertebrae 332a and 332b. The intervertebral foramen 346b provides an opening for one or more of the dorsal root 314b, ventral root 316b, and DRG 320b to extend outwardly from the spinal cord 302 to the environment external to the vertebrae 332a and 332b.

Figure 3E:
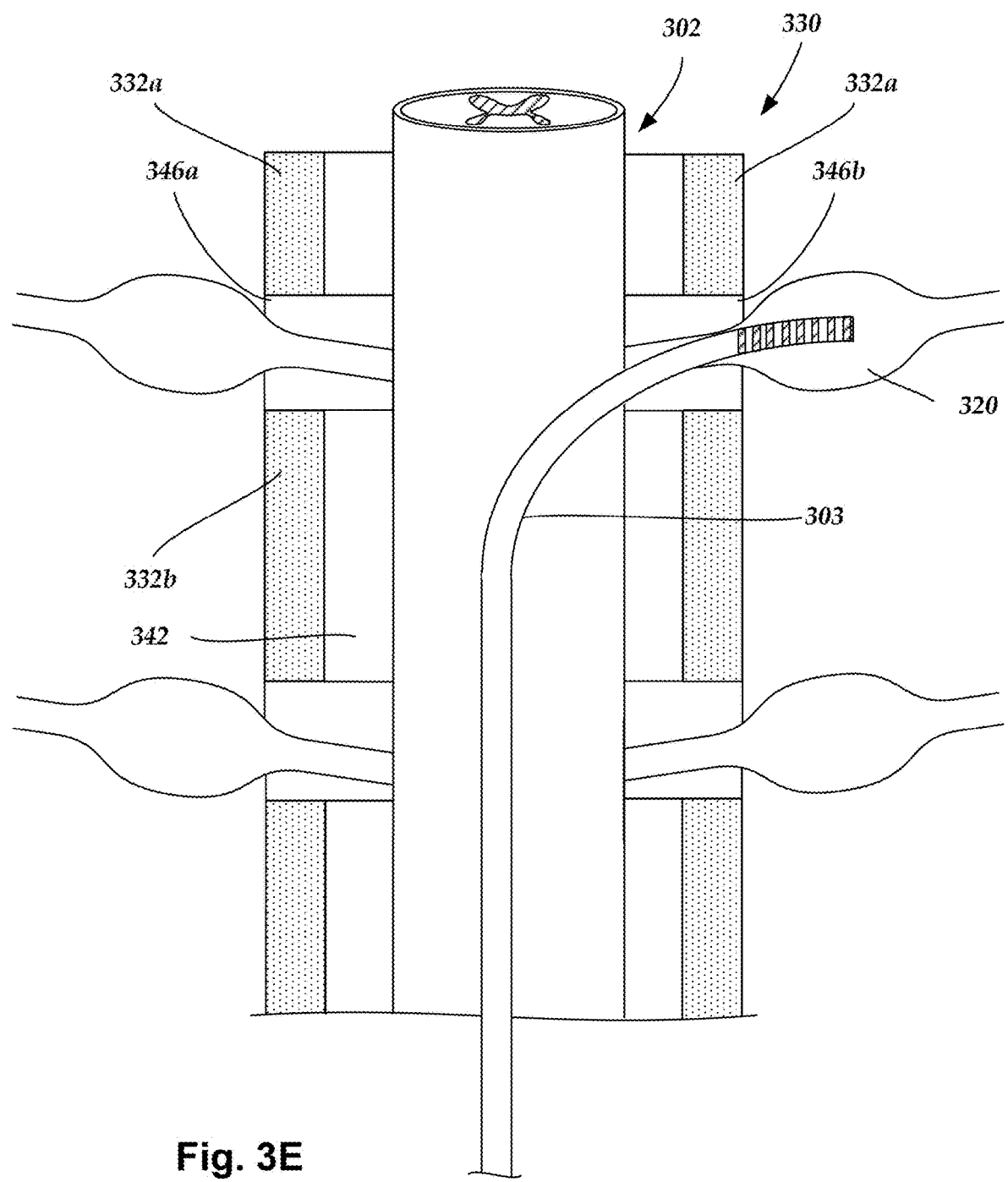
FIG. 3E is a schematic view of one embodiment of a lead inserted through the epidural space to a position adjacent a dorsal root ganglion, according to the invention.

FIG. 3E is a schematic perspective views of the spinal cord 302 disposed along a longitudinal transverse view of a portion of the vertebral column 330. The portion of the vertebral column 330 shown in FIG. 3E includes the vertebrae 332a and 332b and intervertebral foramina 346a and 346b defined between the vertebrae 332a and 332b on opposing sides of the vertebral column 330. A DRG 320 extends outward from one side of the spinal cord 302 and through the intervertebral foramen 346b.

The lead 303 can be advanced out of the epidural space through one of the intervertebral foramen, and for placement near, adjacent, in contact with, or inserted into the desired DRG 320. In at least some embodiments, the lead 303 can be implanted through an introducer (not shown) can also penetrate and extend through the intervertebral foramen 346a during delivery and placement of the lead. In other embodiments, the introducer may only enter the epidural space and the lead 303 is pushed through the intervertebral foramen 346a. Once the lead 303 is placed, the introducer can be removed or backed off.

Figure 4A:
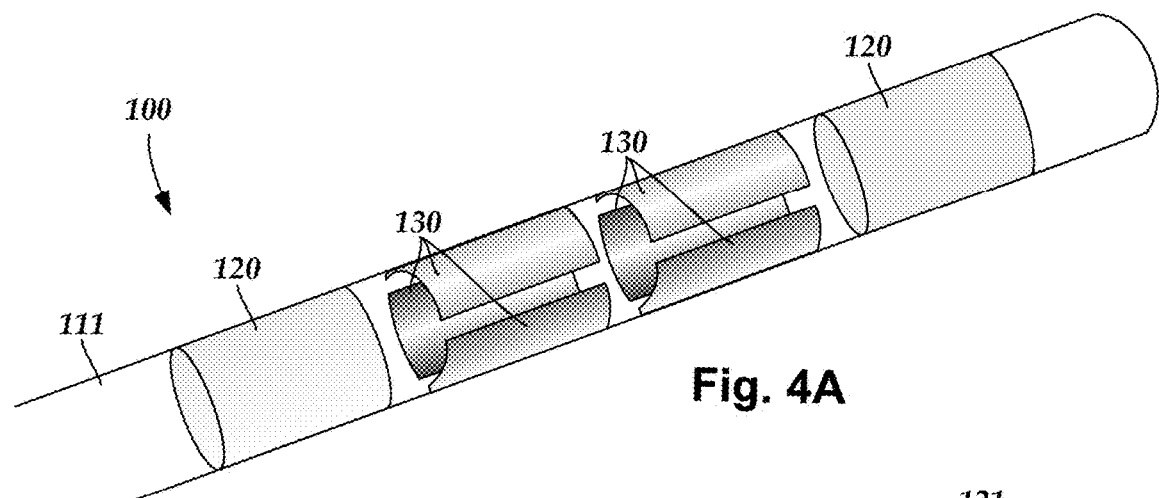
FIG. 4A is a schematic side view of one embodiment of a distal portion of an electrical stimulation lead, according to the invention.
Figure 4B:
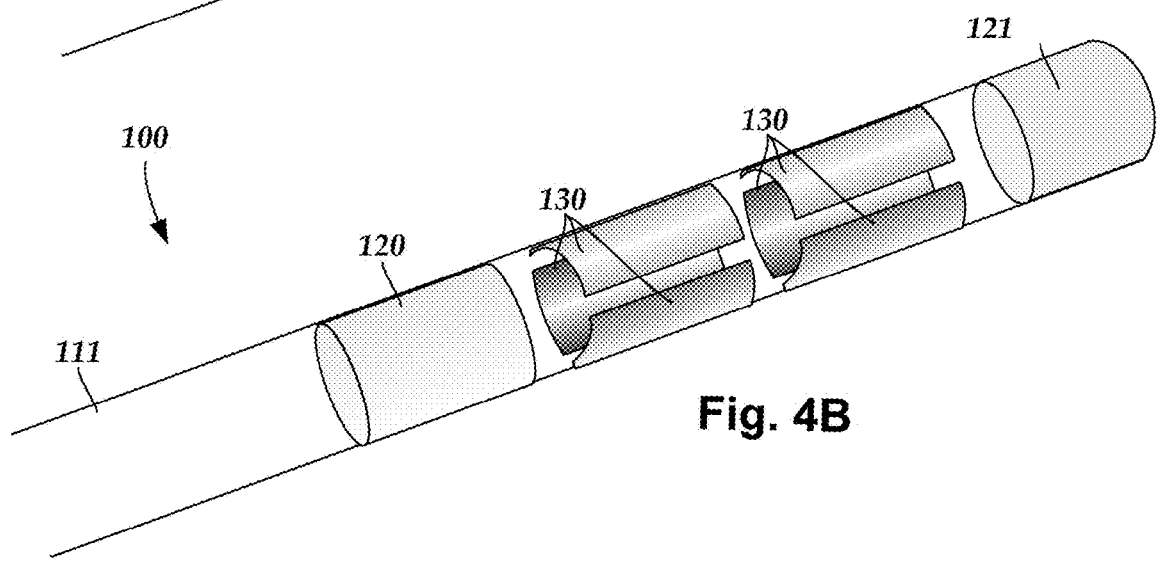
FIG. 4B is a schematic side view of a second embodiment of a distal portion of an electrical stimulation lead, according to the invention.
Figure 4C:
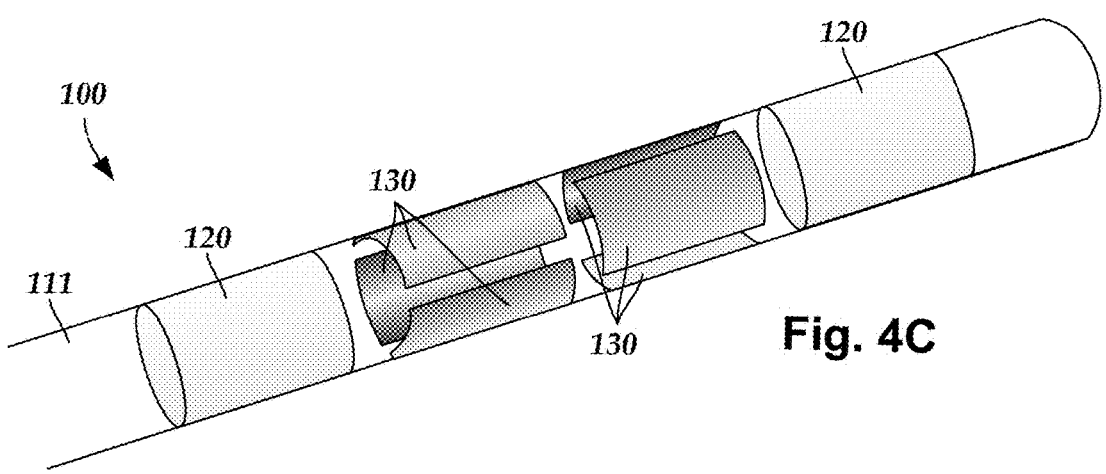
FIG. 4C is a schematic side view of a third embodiment of a distal portion of an electrical stimulation lead, according to the invention.
Figure 4D:
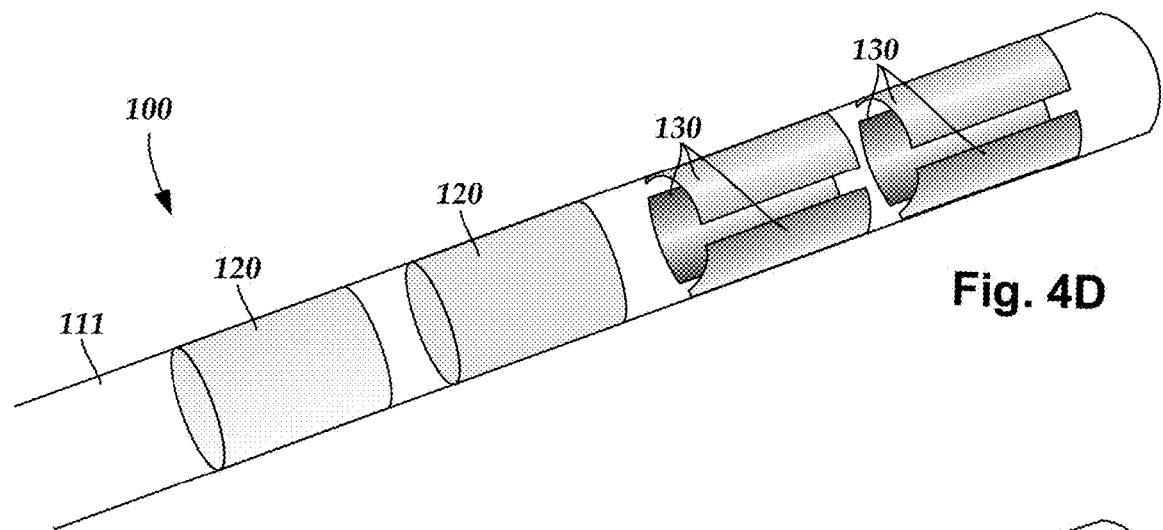
FIG. 4D is a schematic side view of a fourth embodiment of a distal portion of an electrical stimulation lead, according to the invention.
Figure 4E:
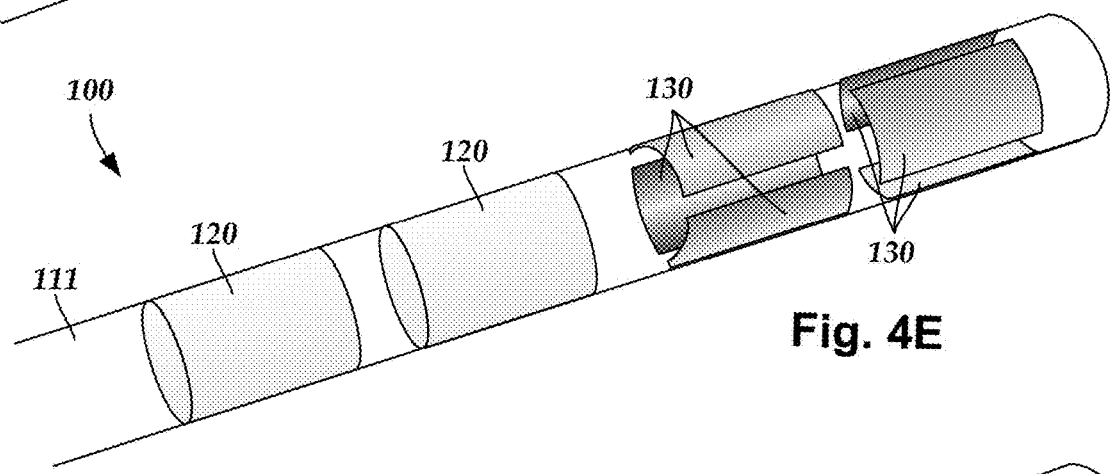
FIG. 4E is a schematic side view of a fifth embodiment of a distal portion of an electrical stimulation lead, according to the invention.
Figure 4F:
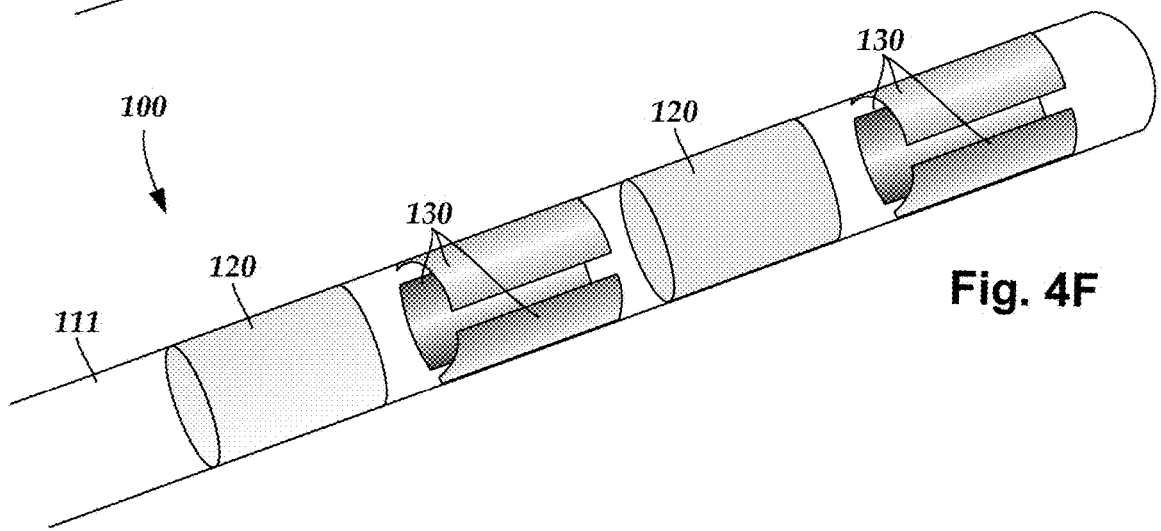
FIG. 4F is a schematic side view of a sixth embodiment of a distal portion of an electrical stimulation lead, according to the invention.
Figure 4G:
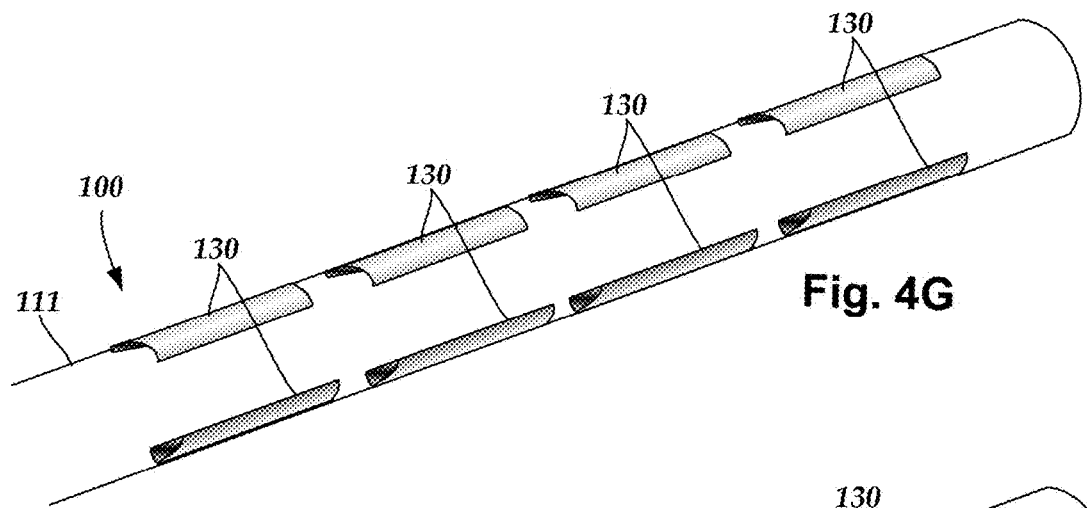
FIG. 4G is a schematic side view of a seventh embodiment of a distal portion of an electrical stimulation lead, according to the invention.
Figure 4H:
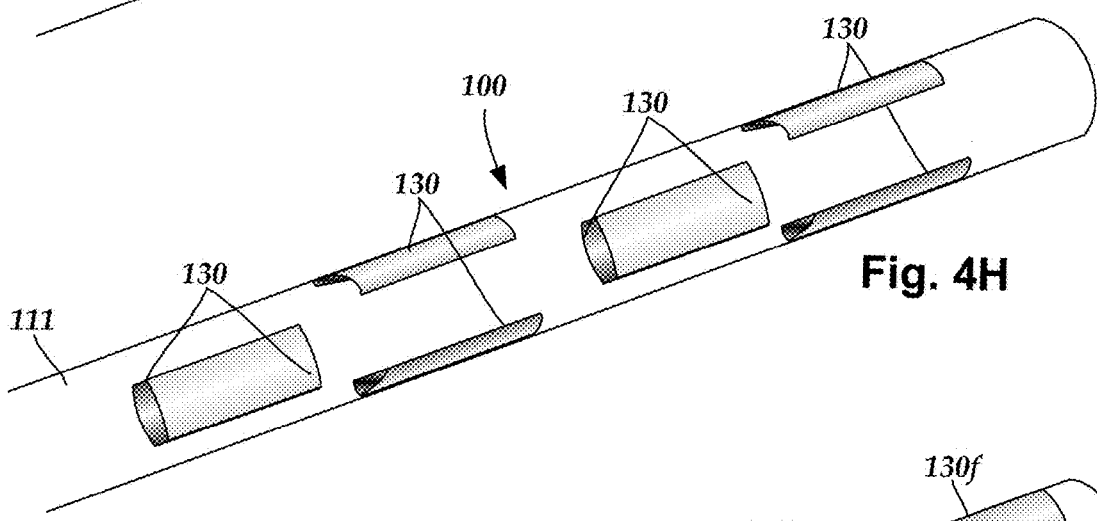
FIG. 4H is a schematic side view of an eighth embodiment of a distal portion of an electrical stimulation lead, according to the invention.

A lead can include ring electrodes, segmented electrodes, tip electrodes, or any other suitable electrode or any combination thereof. A lead containing ring electrodes and segmented electrodes may be arranged in any suitable configuration. FIG. 4A-4I illustrate a variety of different arrangements as non-limiting examples. The arrangements can include ring electrodes 120, 120a, 120b; segmented electrodes 130, 130a-130h; or tip electrodes 121 disposed along a lead body 111. In at least some instances, arrangements of electrodes can be written in a shorthand, starting from the distal end, with each number indicating the number of electrodes at a particular longitudinal position. For example, the arrangement 1-3-3-1, illustrated in FIG. 4A, indicates a ring electrode at the distal-most position, three segmented electrodes at the next position, another three segmented electrodes at the third position, and a ring electrode at the proximal-most position. In addition, if there are multiple, sequential arrangements of the same type "x" can be used. As an example, the arrangement 3x5-1 (or 3x5+1) indicates five sets of three electrodes spaced apart longitudinally starting from the distal end with a single ring electrode at the proximal-most position. Using this notation, the arrangements of the FIGS. 4A-4I can be written as follows: FIG. 4A: 1-3-3-1; FIG. 4B: 1-3-3-1; FIG. 4C: 1-3-3-1; FIG. 4D: 3-3-1-1; FIG. 4E: 3-3-1-1; FIG. 4F: 3-1-3-1; FIG. 4G: 2x4 (or 2-2-2-2); FIG. 4H: 2x4 (or 2-2-2-2); and FIG. 4I: 3x4-2x2 (or 3-3-3-3-2-2).

As non-limiting illustrations of electrode arrangements, when the lead 100 includes two ring electrodes 120 and two sets of segmented electrodes 130, the ring electrodes 120 can flank the two sets of segmented electrodes 130 (see e.g., FIGS. 1B, 4A, 4C). Alternately, the two ring electrodes 120 can be disposed proximal to the two sets of segmented electrodes 130 (see e.g., FIGS. 4D and 4E), or the two ring electrodes 120 can be disposed distal to the two sets of segmented electrodes 130 (not shown) or the two ring electrodes and two sets of segmented electrodes can alternate (see, e.g., FIG. 4F). An arrangement may also include a tip electrode (see, e.g., FIG. 4B) or a single ring electrode 120 either proximal to, distal to, or between the segmented electrodes (not shown). In arrangements with more than two sets of segmented electrodes, the electrodes of the sets may be aligned (see, e.g., FIGS. 4A, 4B, 4D, 4F, 4G, and 4I) or staggered (see, e.g., FIGS. 4C, 4E, and 4H) relative to each other or in any other suitable relative arrangement. By varying the location of the segmented electrodes 130, different coverage of the target neurons may be selected. For example, the electrode arrangements of FIG. 4D or 4E may be useful if the physician anticipates that the neural target will be closer to a distal tip of the lead body 111. Any combination of ring electrodes 120, tip electrode 121, and segmented electrodes 130 may be disposed on the lead 100.

Figure 4I:
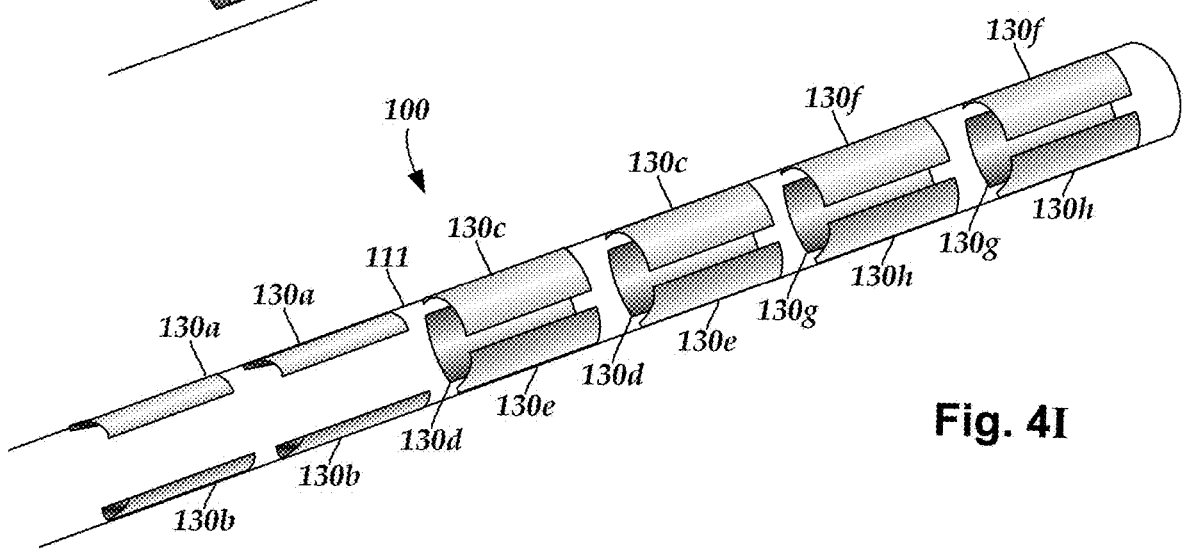
FIG. 4I is a schematic side view of a ninth embodiment of a distal portion of an electrical stimulation lead, according to the invention.

In some embodiments, a lead may only include segmented electrodes 130. For example, FIGS. 4G and 4H illustrate leads with four pairs of segmented electrodes 130 (e.g., a 2x4 arrangement) in aligned (FIG. 4G) or staggered configurations (FIG. 4H). Another arrangement has eight pairs of segmented electrodes 130 (e.g., a 2x8 arrangement—not shown) in aligned or staggered configuration. FIG. 4I illustrates an arrangement in which different types of sets of segmented electrodes 130a-130h are includes—in this case 4 sets of three segmented electrodes 130c-130h and 2 pairs of segmented electrodes 130a, 130b (a 3x4-2x2 arrangement). Another example of a lead with segmented electrodes has the arrangement 3-3-2-3-2-3.

One variation of the arrangement of the lead of FIG. 4I is to electrically gang (i.e., electrically short) segmented electrodes 130a-130h having the same reference numbers (e.g., electrically gang the two segmented electrodes labeled 130a, etc.) Such electrical ganging can be accomplished in any suitable manner including by a conductor attached to the two electrodes within the lead 100 or be electrically coupling the two electrodes to the same channel in the control module. Two, three, or more electrodes can be ganged together. The ganged electrodes provide longer virtual electrodes. In at least some embodiments, the ganged electrodes have an advantage, over very long individual contacts, of maintaining array flexibility while creating a longer virtual electrode. The ganged configuration maintains directionality and array span. Any other arrangement, including any of the arrangements illustrated in FIGS. 4A-4H, can include two or more sets of electrically ganged electrodes. In at least some embodiments, a lead can include electrodes that are electrically ganged and other electrodes that are not ganged together.

In at least some embodiments, one or more of the electrodes include surface features to increase the surface area of the electrodes. Examples of such surface features include dimples, scores, cuts, trenches, grooves, channels, knurls, or other depressions or roughening of the surface.

Figure 5A:
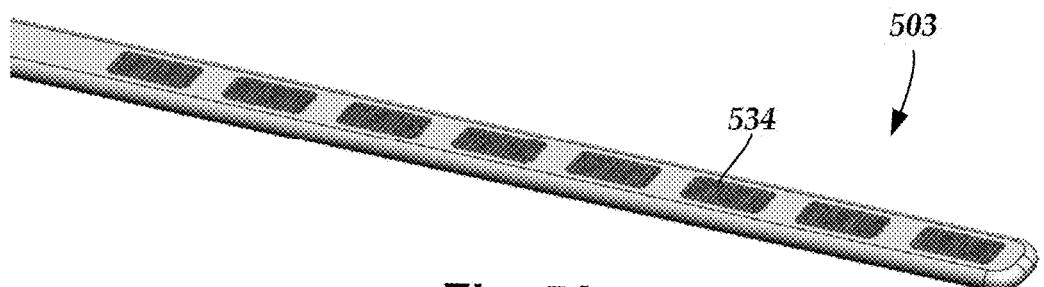
FIG. 5A is a schematic side view of a tenth embodiment of a distal portion of an electrical stimulation lead, according to the invention.
Figure 5B:
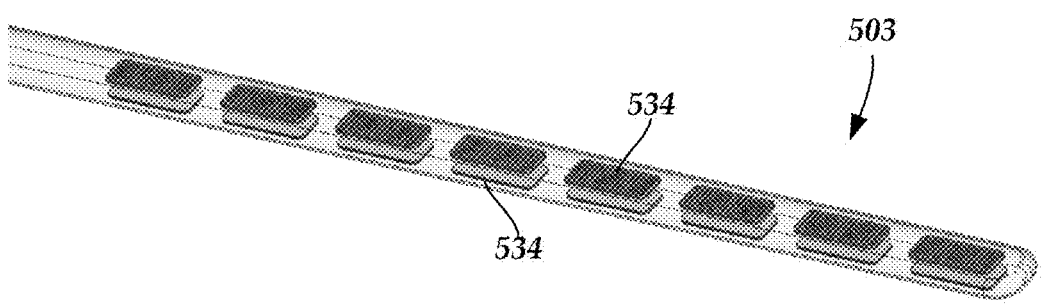
FIG. 5B is a schematic side view of the distal portion of FIG. 5A with the lead body made partially transparent, according to the invention.
Figure 6:
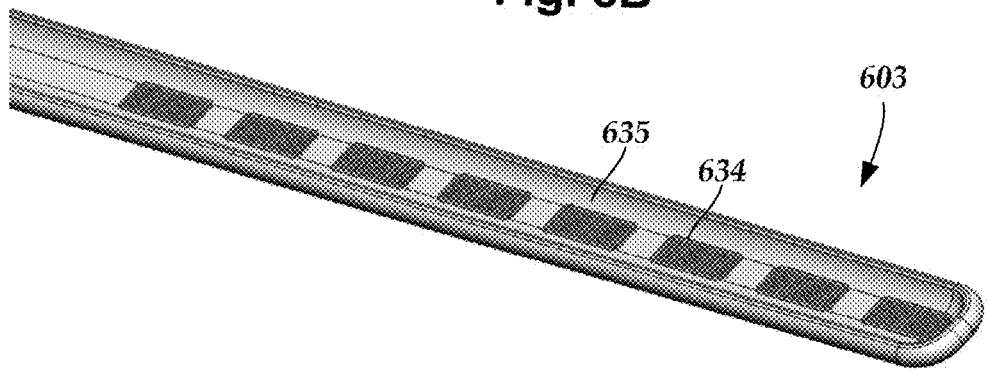
FIG. 6 is a schematic side view of an eleventh embodiment of a distal portion of an electrical stimulation lead, according to the invention.
Figure 7:
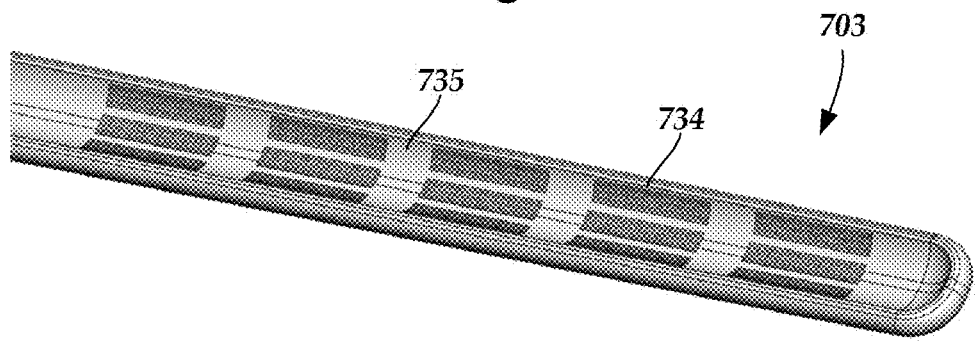
FIG. 7 is a schematic side view of a twelfth embodiment of a distal portion of an electrical stimulation lead, according to the invention.

FIGS. 5A, 5B, 6 and 7 illustrate additional lead configurations. In FIGS. 5A (top view) and 5B (with the lead body partially transparent), at least the distal end of the lead 503 (and optionally all of the lead) is flat with electrodes 534 disposed on one or both (see, in particular, FIG. 5B) sides of the lead. In FIG. 6, at least the distal end of the lead 603 (and optionally all of the lead) forms a trough-like structure 635 with electrodes 634 disposed within the trough-like structure. The lead 700 of FIG. 7 is similar to lead 600 with a trough-like structure 735, except that the electrodes 734 are segmented with sets of two or more segmented electrodes at individual longitudinal positions along the lead. In at least some embodiments, the trough-like structure 635, 735 is shaped to fit around a portion of the dorsal root ganglion. In at least some embodiments, the distal end sections of the leads 500, 600, 700 have a width in range of 0.05 inches (about 1.2 mm) to 0.25 inches (about 6.4 mm) and a thickness in a range of 0.030 inches (about 0.7 mm) to 0.125 inches (about 3.2 mm).

Figure 8:
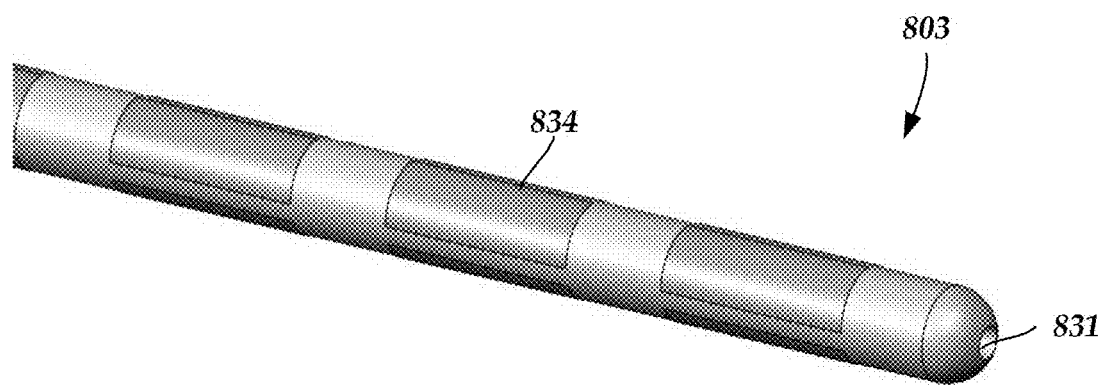
FIG. 8 is a schematic side view of an embodiment of a distal portion of an electrical stimulation lead with a guidewire lumen, according to the invention.

To facilitate delivery and positioning of the lead, in at least some embodiments, the lead 800 includes electrodes 834 and a guidewire lumen 831, as illustrated, for example, in FIG. 8, allowing the lead to be inserted over a guidewire. Techniques for implantation of leads over guidewires are known. In addition, U.S. Provisional Patent Application Ser. No. 62/366,454, incorporated herein by reference in its entirety, describes additional methods of lead implantation utilizing a guidewire.

Figure 9A:
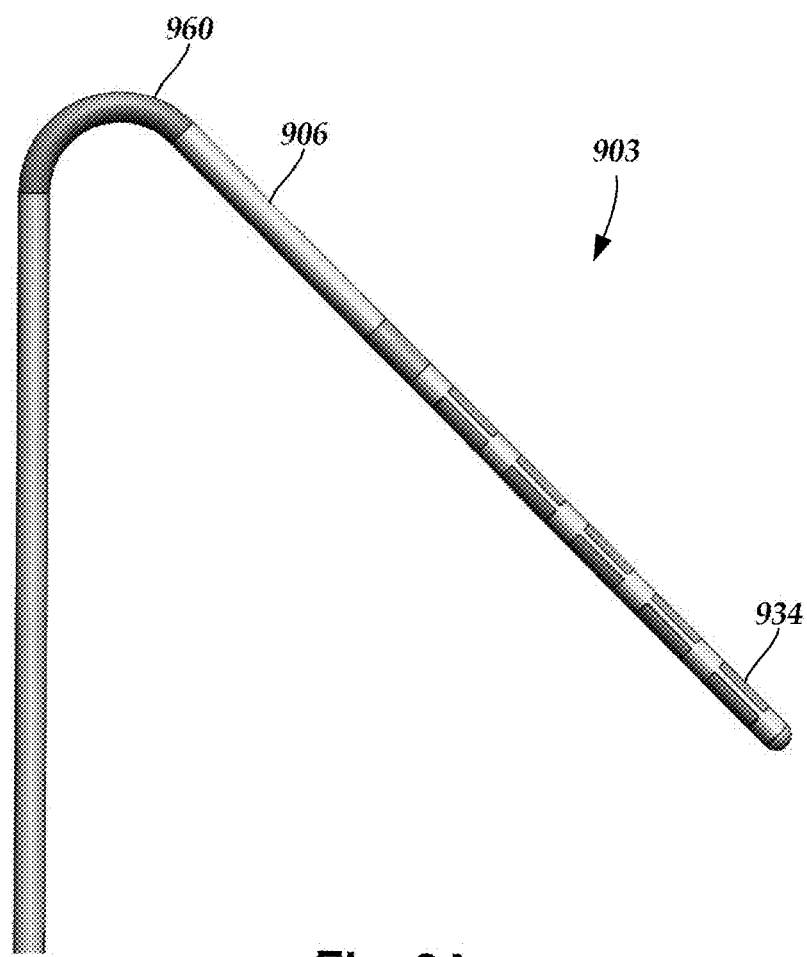
FIG. 9A is a schematic side view of an embodiment of a distal portion of an electrical stimulation lead with a flexible hinge, according to the invention.

FIG. 9A illustrates another embodiment of a lead 900 with electrodes 934, a lead body 906, and flexible hinge 960 proximal to the electrodes. The flexible hinge may be, for example, one or more of an elbow, a joint, a swivel, a hook, a bend, a corner, a turn, or a curve, or any other arrangement that produces a non-zero angle between two adjacent regions of the lead body 906. A lead placed along the DRG may incur a sharp bend as it turns from the epidural space towards the path of the dorsal root. This may place a large stress on the lead body at the bend. While a stiff lead body can be advantageous for lead placement, this is likely to increase the stress at the bend. Including flexible hinge 960 in the lead 900 may allow the lead to traverse the tight bend without excessive stress. Were the entire lead body the same highly bendable design as this section, the lead might not have enough column strength for lead placement.

The flexible hinge 960 can be formed via a variety of methods and structures. For example, the flexible hinge 960 can be formed of a softer durometer of material (or a different, softer or more flexible material) than the lead body 903. In other embodiments, a straight conductor arrangement can be used for other portions (such as the portions of the lead body adjacent the flexible hinge) of the lead and a coiled conductor arrangement for the flexible hinge 960. In another embodiment in which the conductors are coiled along the length of the lead, the coiled conductors can have a wider (more flexible) pitch along the flexible hinge 960 with a narrower, stiffer pitch along portions of the lead body adjacent the flexible hinge. In other embodiments, stiffening elements can be placed in portions of the lead adjacent to the flexible hinge 960, leaving the flexible hinge free of the stiffening elements.

Figure 9B:
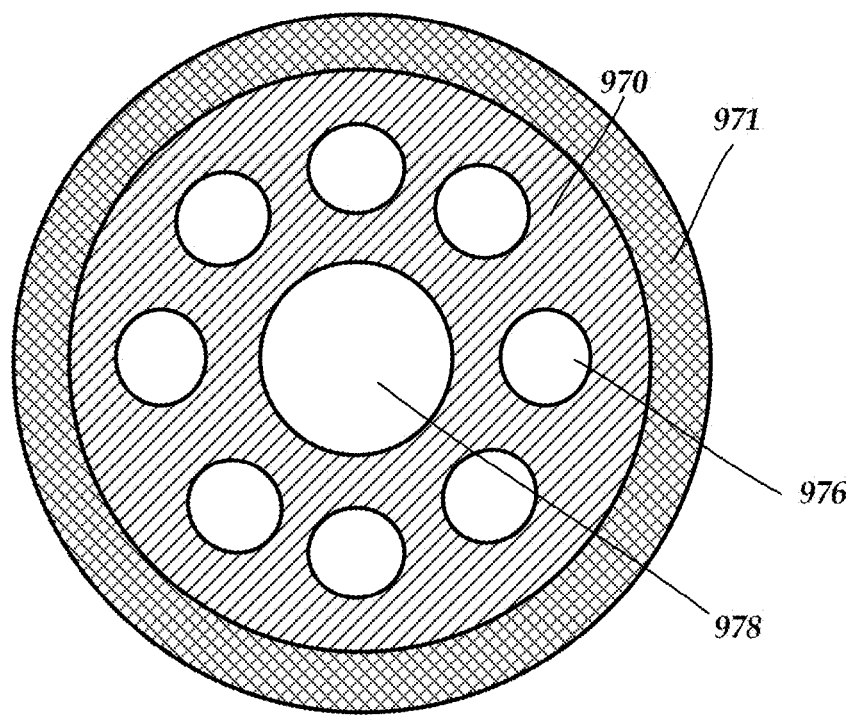
FIG. 9B is a schematic cross-section of one embodiment of a portion of a lead body of an electrical stimulation lead such as the lead of FIG. 9A, according to the invention.
Figure 9C:
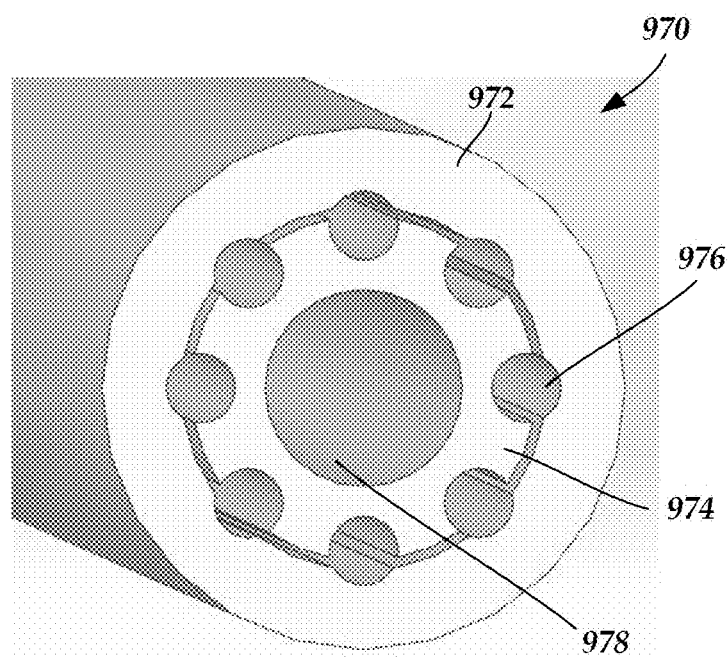
FIG. 9C is a schematic perspective view of one embodiment of a portion of a multi-lumen conductor guide for use in some embodiments of the flexible hinge of the lead of FIG. 9A, according to the invention.

In yet another embodiment, a multi-lumen conductor guide for the conductors can be modified, as illustrated in FIGS. 9B and 9C. The lead body includes a jacket 971 and a multi-lumen conductor guide 970 (which is disposed within the lead body and can extend from the distal end to the proximal end of the lead or over a shorter distance along the lead) that defines a central lumen 978 and multiple conductor lumens 976 which, in the illustrated embodiment, are formed around the central lumen, as illustrated in FIG. 9B. In at least portions of the lead body, the multi-lumen conductor guide is formed as a single piece construction, as illustrated in FIG. 9B. In contrast, as illustrated in FIG. 9C, a flexible hinge can be formed where the multi-lumen conductor guide 970, in the region of the flexible hinge 960 (FIG. 9A), has an inner portion 974 and an outer portion 972 that are separate from each other and can move relative to each other to allow greater movement between the two portions 974, 976 of the multi-lumen conductor guide. In the illustrated embodiment, the inner portion 974 and outer portion 972 are separated along a circumference intersecting each of the conductor lumens 976, but other separation arrangements can also be used.

Figure 9D:
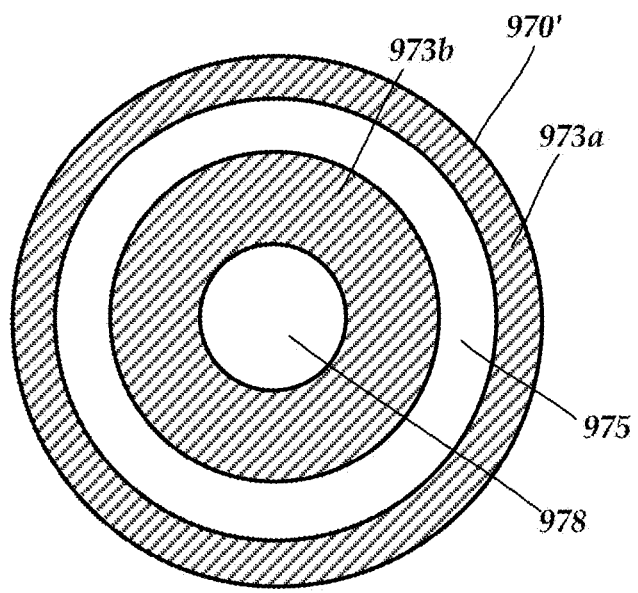
FIG. 9D is a schematic perspective view of another embodiment of a portion of a multi-lumen conductor guide for use in some embodiments of the flexible hinge of the lead of FIG. 9A, according to the invention.

Alternatively, the flexible hinge 960 of the lead may be a region where there is no multi-lumen conductor guide. As another alternative, the flexible hinge 960 can be a region of the multi-lumen conductor guide 970', illustrated in FIG. 9D, that takes the form of two concentric tubes 973a, 973b with a central lumen 978 and an inter-tube lumen 975 between the two tubes within which the conductors extend. In at least adjacent regions to the flexible hinge, the multi-lumen conductor guide 970 has the single-piece form illustrated in FIG. 9B with individual conductor lumens 976.

Figure 9E:
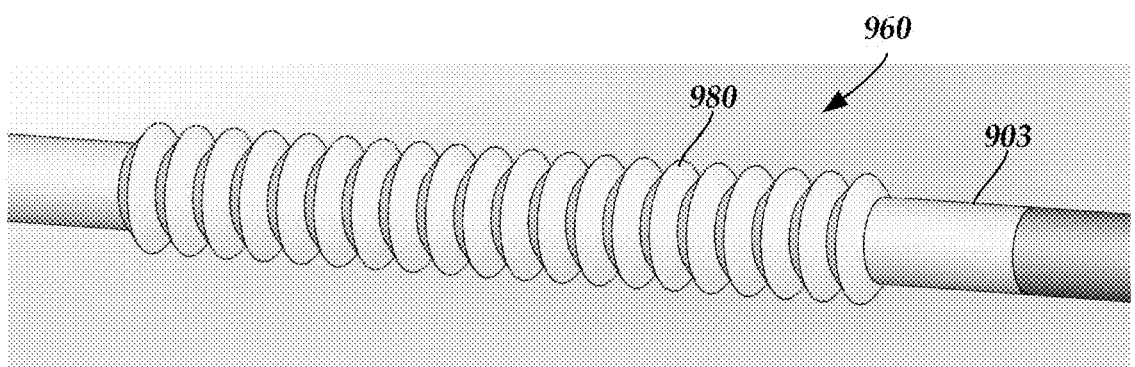
FIG. 9E is a schematic perspective view of another embodiment of the flexible hinge of the lead of FIG. 9A with a bellows-like construction, according to the invention.

In a further embodiment, the flexible hinge 960 can be a bellows-like (or accordion-like) structure 980 formed in the lead body 903 (or a jacket portion of the lead body that is disposed over the multi-lumen conductor guide), as illustrated in FIG. 9E. For example, a bellows-like (or accordion-like) structure can have alternating regions of the lead body with larger and smaller outer diameters, as illustrated in FIG. 9E. In at least some embodiments, the bellows-like (or accordion-like) structure can be expanded or compressed by, for example, pulling or pushing, respectively, on adjacent portions of the lead body. Adjacent regions of the lead body do not have the bellows-like construction.

Figure 9F:
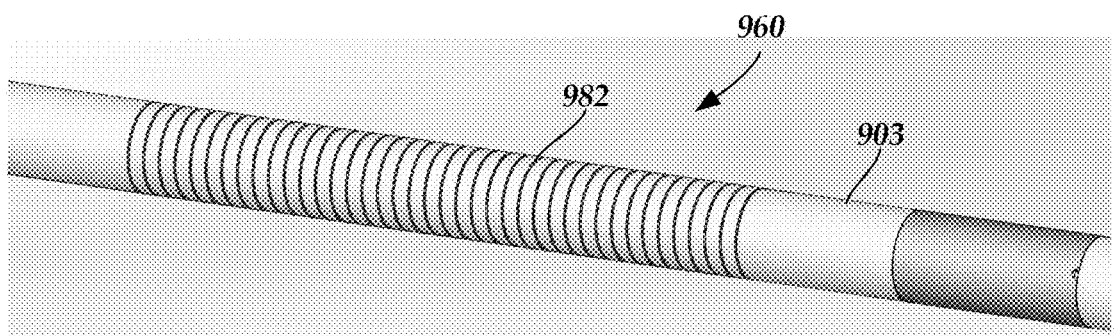
FIG. 9F is a schematic perspective view of another embodiment of the flexible hinge of the lead of FIG. 9A with one or more cuts along the flexible hinge, according to the invention.

In yet another embodiment, the flexible hinge 960 can be formed by one or more cuts 982 in the wall of the lead body 903 and extending along the region of the flexible hinge, as illustrated in FIG. 9F. For example, one or more spiral cuts or multiple circular cuts can be made in the lead body 903. In adjacent portions of the lead body, there are no cuts in the lead body.

All of the methods, features, and structures described above with respect to the flexible hinge 960 can provide increased flexion in the flexible hinge 960 of the lead body 903. It will be understood that any combination of two or more of these methods, features, and structures for the flexible hinge can be used including any combination of the features illustrated in FIGS. 9A-9F or described with respect to those Figures. For example, the flexible hinge may be formed of a lower durometer material and with a bellows-like structure, a two-piece multi-lumen conductor guide, or one or more cuts in the lead body.

When the lead 903 is implanted, the clinician can bend the lead at the flexible hinge 960 to better position the lead relative to the dorsal root ganglion. For example, the flexible hinge may be bent within the epidural space, within the foramen, or outside the foramen and epidural space. In some embodiments, the flexible hinge 960 may be manually bent after retracting the introducer used to implant the lead. In some embodiments, the flexible hinge 960 may automatically bend upon retracting the introducer. For example, the flexible hinge 960 may be made of resilient material that is bent when formed and then straightens when inserted into an introducer or needle for implantation. When the needle or introducer is removed, the flexible hinge then resumes its bent configuration. As another example, shape memory materials may be used in the flexible hinge 960 to cause a bend in the lead upon withdrawal of the introducer. As yet another example, the flexible hinge may be made of material that is stiff outside the body, but when inserted into the body softens (for example, due to the body temperature or contact with body fluids or tissue) and then assumes the bend configuration. In other embodiments, a curved stylet or guidewire may be inserted into the lead to cause a bend at the flexible hinge 960 when the curve in the stylet or guidewire interacts with the flexible hinge. Other methods, tools, and arrangements can be used to assist in bending the flexible hinge.

Figure 10:
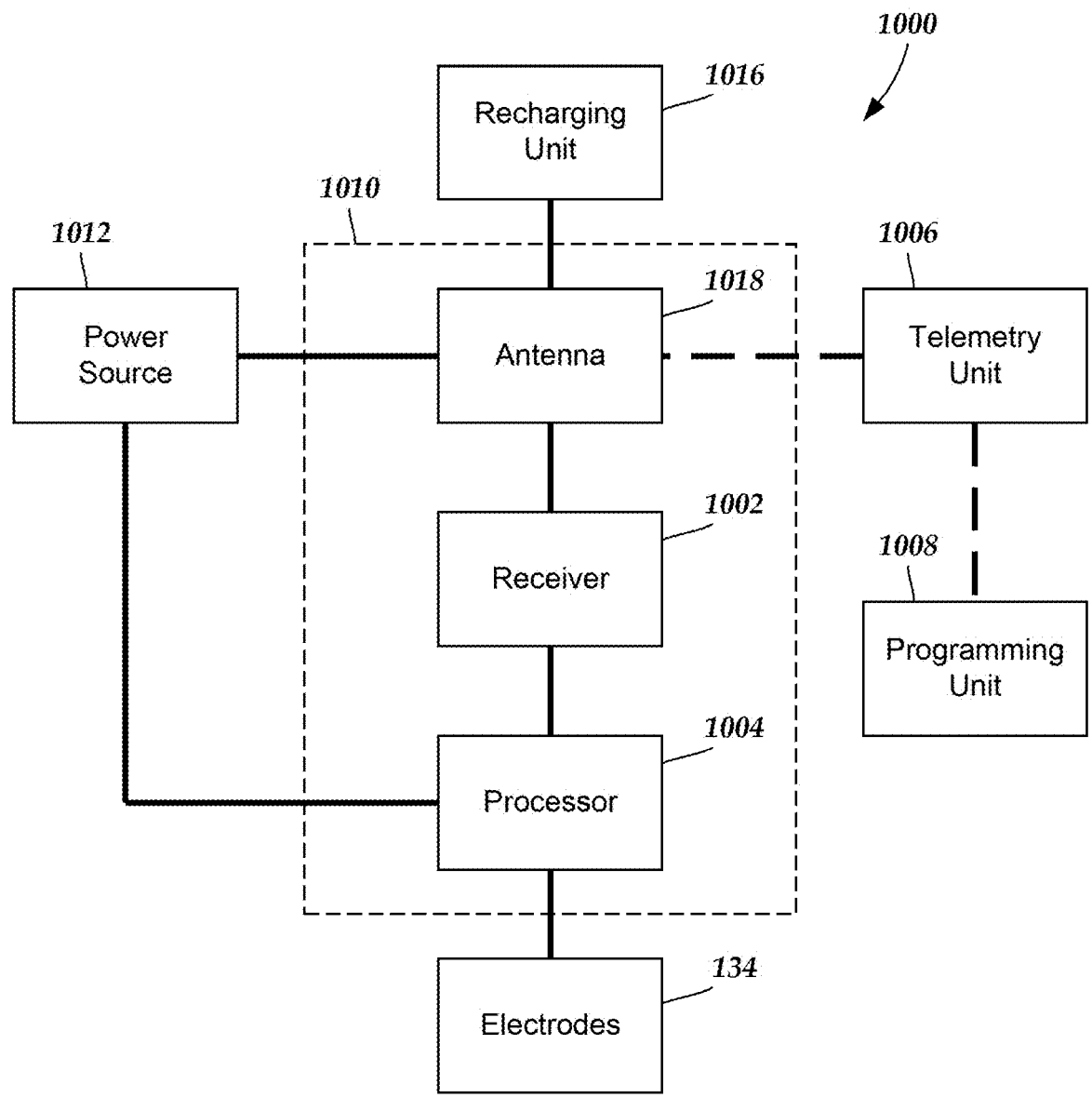
FIG. 10 is a schematic overview of one embodiment of components of an electrical stimulation system, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. patent Ser. No. 10/437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, amplitude, width, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification and examples provide a description of the arrangement and use of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead, the lead comprising:
    a lead body having a proximal portion and a distal portion;
    a plurality of electrodes disposed along the distal portion of the lead body;
    a plurality of terminals disposed along the proximal portion of the lead body;
    a plurality of conductors extending along the lead body and electrically coupling the electrodes to the terminals; and
    a flexible hinge forming part of the distal portion of the lead body and disposed proximal to the electrodes, wherein the flexible hinge is configured as more flexible than adjacent regions of the lead body,
    wherein the lead body comprises a jacket and a multi-lumen conductor guide disposed within the jacket, the multi-lumen conductor guide extending from the proximal portion to the distal portion of the lead body and defining a plurality of conductor lumen through which the conductors extend, wherein, in the flexible hinge, the multi-lumen conductor guide comprises an outer portion and an inner portion that are separate from each other and can move relative to each other, wherein, in the adjacent regions of the lead body, the multi-lumen conductor guide has a single-piece construction.

2. The lead of claim 1, wherein the flexible hinge is formed of a lower durometer material than the adjacent regions of the lead body.

3. The lead of claim 1, wherein the flexible hinge is formed of a different, more flexible material than the adjacent regions of the lead body.

4. The lead of claim 1, wherein the conductors extend straight along the lead body except along the flexible hinge where the conductors are coiled.

5. The lead of claim 1, wherein, except in the flexible hinge, the jacket has a jacket outer diameter and, in the flexible hinge, the jacket comprises alternating first and second sections, wherein the first sections have a first outer diameter and the second sections have a second outer diameter that is larger than the jacket outer diameter and the first outer diameter.

6. An implantable electrical stimulation lead, the lead comprising:
    a lead body having a proximal portion and a distal portion;
    a plurality of electrodes disposed along the distal portion of the lead body;
    a plurality of terminals disposed along the proximal portion of the lead body;
    a plurality of conductors extending along the lead body and electrically coupling the electrodes to the terminals; and
    a flexible hinge forming part of the distal portion of the lead body and disposed proximal to the electrodes, wherein the flexible hinge is configured as more flexible than adjacent regions of the lead body, wherein the lead body comprises a jacket and a conductor guide disposed within the jacket and extending from the proximal portion to the distal portion of the lead body, wherein, in the flexible hinge, the conductor guide comprises two concentric tubes with the conductors disposed between the two concentric tubes and, in the adjacent regions of the lead body, the conductor guide defines a plurality of conductor lumens through which the conductors extend.

7. The lead of claim 1, wherein the lead body has at least one cut in an outer wall of the lead body along the flexible hinge, wherein the lead body is not cut in the adjacent regions of the lead body.

8. The lead of claim 1, further comprising at least one stiffening element in the adjacent regions of the lead body and no stiffening element in the flexible hinge.

9. The lead of claim 1, wherein the conductors are coiled and extend along the lead body, wherein, in the flexible hinge, a pitch of the coiled conductors is wider than in the adjacent regions.

10. The lead of claim 1, wherein the plurality of electrodes comprises a plurality of segmented electrodes.

11. The lead of claim 1, wherein at least part of the distal portion of the lead body upon which the electrodes are disposed is flat.

12. The lead of claim 1, wherein the distal portion of the lead body comprises a concave region within which the electrodes are disposed.

13. The lead of claim 12, wherein the concave region is configured and arranged to fit over a portion of a dorsal root ganglion.

14. The lead of claim 12, wherein the plurality of electrodes comprises a plurality of segmented electrodes arranged in sets of two or more segmented electrodes with each set disposed at a different longitudinal position along the distal portion of the lead body.

15. A method for implanting the lead of claim 1 for stimulation of a dorsal root ganglion of a patient, the method comprising:
    advancing the distal portion of the lead body using an introducer into an epidural space of the patient and through a foramen of the patient to a position near the dorsal root ganglion;
    bending the lead at the flexible hinge; and
    removing the introducer.

16. The method of claim 15, further comprising retracting the introducer to expose the flexible hinge prior to bending the lead at the flexible hinge.

17. A system for electrical stimulation, the system comprising:
    the lead of claim 1; and
    a control module electrically coupleable to the lead.

18. The system of claim 17, further comprising a lead extension electrically coupleable between the lead and the control module.

19. A system for electrical stimulation, the system comprising:
    the lead of claim 6; and
    a control module electrically coupleable to the lead.

20. The lead of claim 6, wherein, except in the flexible hinge, the jacket has a jacket outer diameter and, in the flexible hinge, the jacket comprises alternating first and second sections, wherein the first sections have a first outer diameter and the second sections have a second outer diameter that is larger than the jacket outer diameter and the first outer diameter.

* * * * *